(12) United States Patent
Holzner et al.

(10) Patent No.: US 7,774,080 B2
(45) Date of Patent: Aug. 10, 2010

(54) METHOD FOR MANUFACTURING DENTAL PROSTHESES, METHOD FOR CHECKING A WORKED RAW MATERIAL AREA OR A MANUFACTURING ARRANGEMENT, COMPUTER, COMPUTER PROGRAM, AND MACHINE-READABLE MEDIUM

(75) Inventors: Stephan Holzner, Hohenschäftlarn (DE); Gerhard Weber, Inning/Ammersee (DE)

(73) Assignee: Institut Straumann AG, Basel (CH)

( * ) Notice: Subject to any disclaimer, the term of this patent is extended or adjusted under 35 U.S.C. 154(b) by 188 days.

(21) Appl. No.: 11/486,980

(22) Filed: Jul. 13, 2006

(65) Prior Publication Data

US 2007/0048689 A1 Mar. 1, 2007

(30) Foreign Application Priority Data

Jul. 28, 2005 (DE) ................ 10 2005 035 474

(51) Int. Cl.
G06F 19/00 (2006.01)
A61C 13/00 (2006.01)
(52) U.S. Cl. .............. 700/97; 700/171; 433/201.1
(58) Field of Classification Search ........... 700/95–98, 700/117–119, 28, 159, 170, 171, 186–195; 433/167, 199.1–212.1; 72/324–341; 29/896.1, 29/896.11
See application file for complete search history.

(56) References Cited

U.S. PATENT DOCUMENTS

| | | | | |
|---|---|---|---|---|
| 5,224,049 A | * | 6/1993 | Mushabac | 700/163 |
| 5,378,154 A | * | 1/1995 | Van Der Zel | 433/223 |
| 5,934,163 A | * | 8/1999 | Saunders et al. | 82/168 |
| 6,089,713 A | * | 7/2000 | Hof et al. | 351/169 |
| 6,287,119 B1 | * | 9/2001 | van Nifterick et al. | 433/213 |
| 6,287,121 B1 | * | 9/2001 | Guiot et al. | 433/218 |
| 6,298,279 B1 | * | 10/2001 | Shimada et al. | 700/182 |
| 6,299,953 B1 | * | 10/2001 | Meier et al. | 428/36.92 |
| 6,454,629 B1 | * | 9/2002 | Basler et al. | 451/5 |
| 6,580,963 B2 | * | 6/2003 | Susnjara | 700/171 |
| 6,690,990 B1 | * | 2/2004 | Caron et al. | 700/171 |
| 6,835,066 B2 | | 12/2004 | Iiyama et al. | |
| 6,868,303 B1 | * | 3/2005 | Chabirand Garconnet et al. | 700/135 |

(Continued)

FOREIGN PATENT DOCUMENTS

CA 2521241 10/2004

(Continued)

Primary Examiner—M. N. Von Buhr
(74) Attorney, Agent, or Firm—IP Strategies

(57) ABSTRACT

The invention relates to a method for manufacturing dental prostheses, wherein from a raw material area, such as a blank, a dental prosthesis is manufactured (milled out) at a manufacturing position, such as a milling position, the manufacturing position of one or more dental prostheses being determined on the basis of one or more predetermined criteria. Furthermore, the invention relates to a method for checking a worked raw material area and/or a manufacturing arrangement for a raw material area, wherein it is checked whether one or more manufacturing shapes can still be manufactured from a number of predetermined manufacturing shapes. Moreover, the invention relates to a method for manufacturing a dental prosthesis, wherein from a raw material area a dental prosthesis is manufactured, wherein a raw material is selected from a plurality of raw material areas on the basis of one or more predetermined criteria. Moreover, the invention relates to a corresponding computer, a computer program, and a machine-readable medium.

24 Claims, 23 Drawing Sheets

U.S. PATENT DOCUMENTS

| | | | |
|---|---|---|---|
| 6,917,848 B1 * | 7/2005 | Nakayama et al. | 700/121 |
| 6,979,496 B2 * | 12/2005 | Haymann et al. | 428/542.8 |
| 7,020,972 B2 * | 4/2006 | Graf et al. | 33/501.7 |
| 7,089,082 B1 * | 8/2006 | Lukis et al. | 700/182 |
| 7,107,233 B2 * | 9/2006 | Des Champs | 705/26 |
| 7,123,986 B2 * | 10/2006 | Lukis et al. | 700/197 |
| 7,431,545 B2 * | 10/2008 | Suttor et al. | 409/132 |
| 2004/0072121 A1 * | 4/2004 | Filser et al. | 433/25 |
| 2004/0106087 A1 * | 6/2004 | Weigl et al. | 433/218 |
| 2004/0236459 A1 * | 11/2004 | Clayton et al. | 700/171 |
| 2005/0003329 A1 | 1/2005 | Lehmann et al. | |
| 2005/0122346 A1 * | 6/2005 | Horn | 345/629 |
| 2006/0063135 A1 * | 3/2006 | Mehl | 433/223 |
| 2006/0105294 A1 * | 5/2006 | Burger et al. | 433/167 |
| 2006/0111806 A1 * | 5/2006 | Kraemer et al. | 700/117 |
| 2007/0218426 A1 * | 9/2007 | Quadling et al. | 433/223 |
| 2007/0275352 A1 * | 11/2007 | Gubler et al. | 433/201.1 |
| 2009/0181346 A1 * | 7/2009 | Orth | 433/201.1 |

FOREIGN PATENT DOCUMENTS

| | | |
|---|---|---|
| DE | 19944130 A1 | 4/2001 |
| DE | 10203665 A1 | 11/2002 |
| DE | 10313690 A1 | 11/2004 |
| EP | 1658825 A1 | 5/2006 |
| JP | 05042380 A * | 2/1993 |
| WO | WO-2004084756 | 10/2004 |
| WO | WO-2004086999 A1 | 10/2004 |
| WO | WO-2005007007 A2 | 1/2005 |

* cited by examiner

Check a worked raw material area and/or a manufacturing arrangement for a raw material area Determine whether, from a number of predetermined manufacturing shapes, any one or more of the predetermined manufacturing shapes can be manufactured from the worked raw material area

Fig. 21

Determine whether, from a number of predetermined manufacturing shapes, any one or more of the predetermined manufacturing shapes can be manufactured from the worked raw material area Decide whether the worked raw material area or the manufacturing arrangement is rated as "full" or "not yet full"

Fig. 22

METHOD FOR MANUFACTURING DENTAL PROSTHESES, METHOD FOR CHECKING A WORKED RAW MATERIAL AREA OR A MANUFACTURING ARRANGEMENT, COMPUTER, COMPUTER PROGRAM, AND MACHINE-READABLE MEDIUM

BACKGROUND OF THE INVENTION

The invention relates to two methods for manufacturing dental prostheses, a method for checking a worked raw material area and/or a manufacturing arrangement as well as a computer, a computer program and a machine-readable medium.

From WO 02/39056 A1, it is known to digitally detect the shapes of remaining tooth areas by means of patterns and to generate the shapes of dental prostheses on the basis thereof with the aid of software. The shape data of dental prostheses obtained in the process can subsequently be used for manufacturing the dental prostheses, for example by milling or laser lithography.

All of these cases are single-piece productions as each dental prosthesis is individually and only once fabricated for the individual remaining tooth area.

BRIEF SUMMARY OF THE INVENTION

It is the object of the present invention to provide a method for manufacturing dental prostheses, a method for checking a worked raw material area and/or a manufacturing arrangement, as well as a computer, a computer program and a machine-readable medium by which a large number of dental prostheses can be manufactured as optimally as possible.

This object is achieved by a method according to claim 1, a method according to claim 15, a method according to claim 18, a computer according to one of claims 21 to 23, a computer program according to claim 24, and a machine-readable medium according to claim 25.

Advantageous embodiments are disclosed in the subclaims.

In the method, the manufacturing position of one or more dental prostheses is determined on the basis of one or more predetermined criteria. This can be best performed all-automatically with a computer.

The manufacturing position on the one hand results from the orientation of the manufacturing location (to be changed by rotation) in the raw material area as well as from the position of the manufacturing location (to be changed by shifting). Tilting is also possible.

One possible manufacturing process is, for example, milling out of a blank. In the process, a manufacturing shape, i.e. a milling shape, is milled out of a raw material area, i.e. a blank, at a manufacturing position, i.e. a milling position.

However, other methods, such as construction methods, can also be employed as manufacturing methods, such as laser lithography, where the respective uppermost layer of a powdery material that is applied layer by layer is worked with a laser. The laser irradiation can locally melt the powdery material and harden it to form a dental prosthesis. Here, the raw material area is the area where the raw material (e.g. the powdery material) can be located, so that it can be processed to form a dental prosthesis.

The consideration of one or more predetermined criteria permits purposeful optimisations of the manufacturing process that show effects in case of a great number of dental prostheses to be manufactured.

It is, for example, possible to fix the manufacturing position in the raw material area such that as many dental prostheses as possible can be manufactured from the raw material area. It is also possible that the manufacturing process is as fast as possible or that shape/remaining size of the unworked raw material area remains such that presumably as many dental prostheses as possible can still be manufactured from the raw material area. Furthermore, the stability of the raw material area can be considered. For example, during milling out from a blank, the stability of the blank with respect to deformation by the milling working can be considered.

Further, depending on the type of the dental prosthesis, for example, a varying precision of the manufactured part can be desired which can vary depending on the position of the manufacturing position. In laser lithography, there are areas where focussing is particularly sharp and thus high precision is achieved, while the precision in other areas is not as high. In milling, too, the precision at the edge of the blank, where it is held firmly, will be higher than in other areas, where it can somewhat deform.

Advantageously, the manufacturing position is therefore determined by means of one or more different criteria. These can be, for example, the manufacturing position of one or more other dental prostheses in the raw material area, the manufacturing shapes of dental prostheses still to be manufactured and which have not yet been associated to a raw material area, shape or remaining size, respectively, of the unworked area of a raw material area after manufacture, the distance to one or more of other manufacturing positions of dental prostheses in the raw material area, the manufacturing time, the overlap of marginal manufacturing areas between various manufacturing positions, the type of material of the raw material/blank, and/or the type of the dental prosthesis. Further criteria are possible.

By the determination of the manufacturing position, for example, on the basis of the manufacturing position of other dental prostheses or on the basis of the shape and/or remaining size of the unworked areas of the raw material area and/or the distance to one or more of other manufacturing positions of other dental prostheses or the overlap of marginal manufacturing areas, it can be possible to accommodate the manufacturing positions of as many dental prostheses as possible in one single raw material area. These can be milled out immediately one after the other, or else with the raw material area being taken out of a manufacturing machine in between. By optimising the arrangement of the manufacturing positions, it is possible to manufacture as many dental prostheses as possible using as little material as necessary.

Taking into consideration the expected manufacturing time, a manufacturing process as fast as possible can also be achieved. If, for example, a change of milling tools is necessary, the position of the dental prosthesis on the blank affects the milling time. If the distances between the milling position and the tool change position are relatively long, the cutter head has to reciprocate for relatively long times which affects the milling time. In laser lithography, too, the manufacturing time varies at different locations within the raw material area.

In order to mill a dental prosthesis out of a blank, a milling tool has to mill a certain gap between the dental prosthesis and the rest of the blank. In the gap, there are possibly still webs bridging the gap for supporting the dental prosthesis. The milling area is thus larger than the extension of the dental prosthesis, as the dental prosthesis has to be surrounded outside by the above-mentioned gap. This gap is referred to as marginal milling area or marginal manufacturing area. If the marginal milling areas overlap between the various dental prostheses, this is not very harmful but can be advantageous for optimally utilizing the blank. In laser lithography, certain minimum distances between two dental prostheses also have to be observed in order to avoid an unintended connection between two dental prostheses. Each manufacturing shape is thus also surrounded by a marginal manufacturing area where no laser working of powder must take place.

Due to the milling out of dental prostheses, the blank loses stability. It can therefore be advantageous to consider this when the milling position is determined in order to be able to utilize good blank stability even when the last dental prostheses or else already the second or third dental prosthesis are milled. If the blank is, for example, clamped at its edge, an instable blank can easily flutter somewhat leading to imprecise dental prostheses. This can be relevant in particular depending on the type of dental prosthesis.

The mentioned or else other criteria can be taken into consideration with various weighting factors depending on the importance.

The determination of the manufacturing position is advantageously performed with a computer. This permits the simultaneous consideration of several or many criteria with reproducible results. The relevant criteria can have been selected by an operator or else been selected automatically. A self-learning system, where the criteria are automatically weighted with various factors and these factors are adapted on the basis of the end results, e.g. with respect to the utilization of the raw material area, can be almost exclusively realized with a computer. Further, a computer permits high processing speed and therefore relatively high data throughput rates. For determining the manufacturing position, various of the mentioned criteria can therefore as a rule only be considered with a computer.

The positioning of the webs for supporting the dental prosthesis during and after milling is advantageously also performed by means of one or more predetermined criteria. This permits an automatic positioning of the webs. Here, particularly relevant criteria are the stability of the position of the dental prosthesis during milling and the stability of the blank, respectively, in particular in the area of the webs. During milling, the blank has to be supported by the webs such that it moves or is deformed as little as possible under the mechanical influence of the cutter head. The stability of the position of the dental prosthesis is only provided by the webs in this case. Furthermore, it has to be considered at which location the webs end in the blank as a web that is supported at an instable part of the blank cannot impart any stability to the dental prosthesis during milling.

The positioning and/or the number of webs is best performed automatically with a computer.

The various criteria for arranging the webs or for determining their number can also be considered with various weighting factors.

It is advantageously possible to determine a manufacturing position after another dental prosthesis has already been manufactured from the raw material area. This permits an immediate determination of the position, so that afterwards one can directly start the manufacture. This is an advantage in case of urgent orders. On the other hand, it is advantageous to determine the manufacturing position of several dental prostheses before one of them is manufactured from the raw material area, as then both manufacturing positions can be optimally adjusted with respect to one another. For doing so, however, one has to wait until at least two orders for dental prostheses are received. Otherwise, the adjustment of the manufacturing position of a dental prosthesis is only possible by means of the predetermined manufacturing position of the other dental prosthesis.

A method in which one first tries to completely fill one raw material area with the manufacturing positions of several dental prostheses is particularly advantageous. Only when the raw material area is largely completely utilized, i.e. most probably no further manufacturing positions can be arranged thereon, the raw material area is worked, i.e. the blank is, for example, milled or a laser lithography method is performed. This has the advantage that the raw material area can be optimally utilized altogether as the relative position of all dental prostheses relative to one another can be optimised with respect to the raw material area yield. In the process, other relevant criteria can also be considered.

A method in which from a number of dental prostheses those prostheses to be manufactured that result in a utilization of the raw material area as good as possible are selected is particularly advantageous. Thus, for example, ten of fifteen dental prostheses to be manufactured which can be optimally arranged in the raw material area can be selected.

In the method, advantageously the ratio of blank surface to milled surface and/or unmilled surface can be determined. This can be taken as a measure of how well a blank was utilized. Moreover, the ratio of raw material volume to volume to be worked and/or unworked volume can be determined and taken as measure of utilization. Moreover, the surface of a projection of the worked volume to a plane being in parallel to the applied powder layers or a blank surface can be determined in comparison to the surface of such a plane and possibly taken as utilization factor.

Moreover, the dental prostheses to be manufactured can be weighted with predetermined values and the sum of these weighted values can be formed. This sum can be taken for a predetermined raw material area type as measure for the utilization of the raw material area.

The mentioned procedure steps for determining the utilization of the raw material area can be taken for determining the manufacturing position. Furthermore, they can be taken for evaluating the effected determinations of manufacturing positions. With this evaluation, for example, the weighting of the various criteria can be optimised when the manufacturing position is determined, like with a self-learning system.

In a method for checking a worked raw material area or a manufacturing arrangement for a raw material area, respectively, it is checked whether from a plurality of predetermined manufacturing shapes one or more manufacturing shapes can still be manufactured. With an already partly worked raw material area, the method can be employed for checking whether the raw material area is full or not yet full. A full raw material area can be rejected as no further dental prostheses can be manufactured therefrom. Instead of checking a raw material area from which dental prostheses have already been manufactured, a manufacturing arrangement for a raw material area can also be checked. Such a manufacturing arrangement is composed of various manufacturing positions of various dental prostheses which can be manufactured from a raw material area in the given arrangement.

During milling, for example, partly worked blanks can be stored and reused later. In laser lithography, containers in which the construction is performed can be removed from the laser lithography device and reinserted later. By doing so, one can manufacture another dental prosthesis above and/or next to an already manufactured dental prosthesis.

The given manufacturing shapes can be those of dental prostheses still to be manufactured, however, they can also be given standard shapes. By means of predetermined standard shapes, for example, an already worked raw material area can be checked on the basis of objective criteria to find out whether it makes sense to further store the raw material area in order to possibly manufacture dental prostheses from it later or to reject the raw material area.

A method for manufacturing a dental prosthesis consists in selecting an individual raw material area from which the dental prosthesis is to be manufactured from a plurality of raw material areas.

This method makes sense if, for example, several raw material areas from which the dental prosthesis can be manufactured are available. If the various raw material areas are, for example, already partly worked, on the basis of the worked areas of the various raw material areas, a varying utilization of the raw material areas can result from a positioning of the manufacturing position of the dental prosthesis to be manufactured in the various raw material areas. The selection of the raw material area in which an optimal utilization results is therefore advantageous in this case.

The number of available raw material areas can be another criterion. If already a large number of raw material areas from which possibly only one dental prosthesis can be manufactured is stored, it can be advantageous to mill out a dental prosthesis not optimally utilizing a raw material area if thus the raw material area can be rejected to provide space in the raw material area storage. If, for example, no blank of an appropriate thickness exists, a blank of a greater thickness can be selected. If no laser lithography container in which optimal utilization is possible with the still available construction height in the container is available, it can also be advantageous to use a container that is not optimally utilized if then all already manufactured dental prostheses can be withdrawn from the container and used.

If a raw material area is just located in a manufacturing machine, it can also be advantageous to select this raw material area as then one can directly start the manufacture of the dental prosthesis. This possibly permits short working times in case of very urgent manufacturing orders.

The raw material areas, i.e., for example, the containers of the laser lithography method or the blanks, are advantageously automatically transported from a storage to the manufacturing machine (laser lithographer, milling machine) and possibly back again. This on the one hand prevents misoperations and permits an operation as cheap as possible. To this end, for example, a robot and/or automated transporting plants can be employed.

Furthermore, a computer, a computer program, and a machine-readable medium are provided for performing the mentioned methods.

BRIEF DESCRIPTION OF THE DRAWINGS

Advantageous embodiments are to be illustrated with reference to the enclosed drawings, wherein:

FIGS. 7-25 are flow diagrams illustrating different aspects of the method of the invention;

DETAILED DESCRIPTION OF THE INVENTION

In the following Figures, the milling method is described representatively of generally one manufacturing method. However, the embodiments also correspondingly apply to other manufacturing processes, such as laser lithography.

Figure 1A:
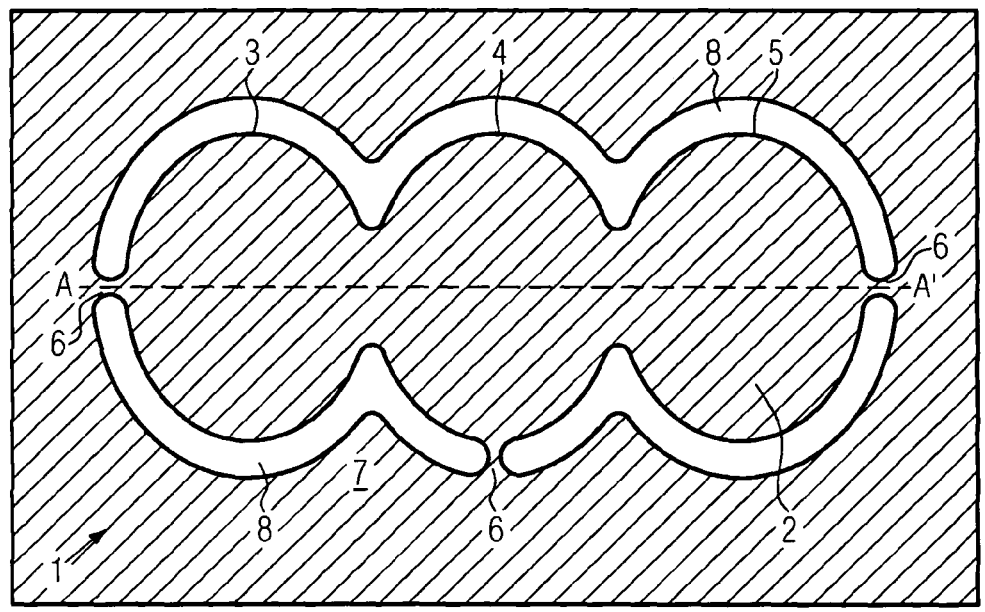
FIG. 1a shows a plan view of a dental prosthesis in a blank.
Figure 1B:
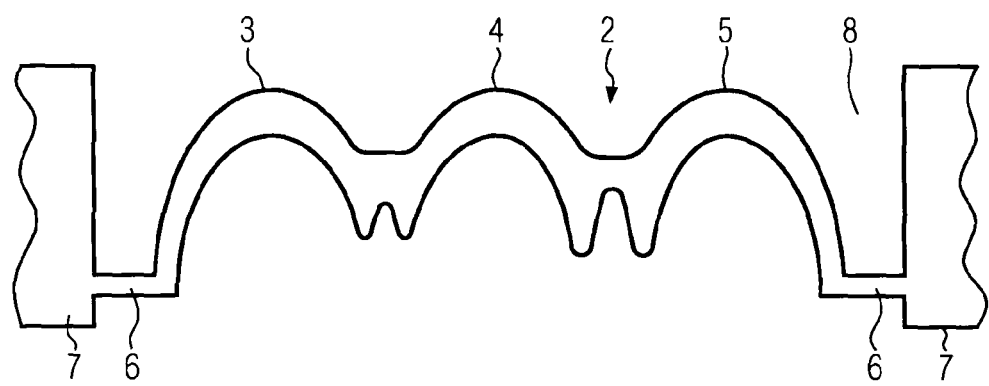
FIG. 1b shows a lateral section of a dental prosthesis in a blank.

In FIGS. 1a and 1b, a milled out dental prosthesis is shown in a plan view and in a lateral section. FIG. 1b corresponds to the section along line A-A' in FIG. 1a. The shown dental prosthesis is a three-membered dental prosthesis composed of the three members 3, 4, 5. Each member corresponds to a teeth position in a jaw. The dental prosthesis 2 is still connected to the blank 7 by the webs 6. The rest of the dental prosthesis 2 is milled out. The webs 6 are located in the marginal milling area 8, i.e. the area in which milling is performed, where, however, there is no portion of the dental prosthesis 2. This marginal milling area 8 (not in shaded line) surrounds the dental prosthesis 2 as can be seen in FIG. 1a in a plan view. The outer boundary of the marginal milling area 8 defines the boundary of the area within which the blank is worked by milling. The boundary determines the milling shape. The milling shape represented in FIG. 1a can be arranged on a blank 7 in various orientations or positions, respectively.

Figure 2:
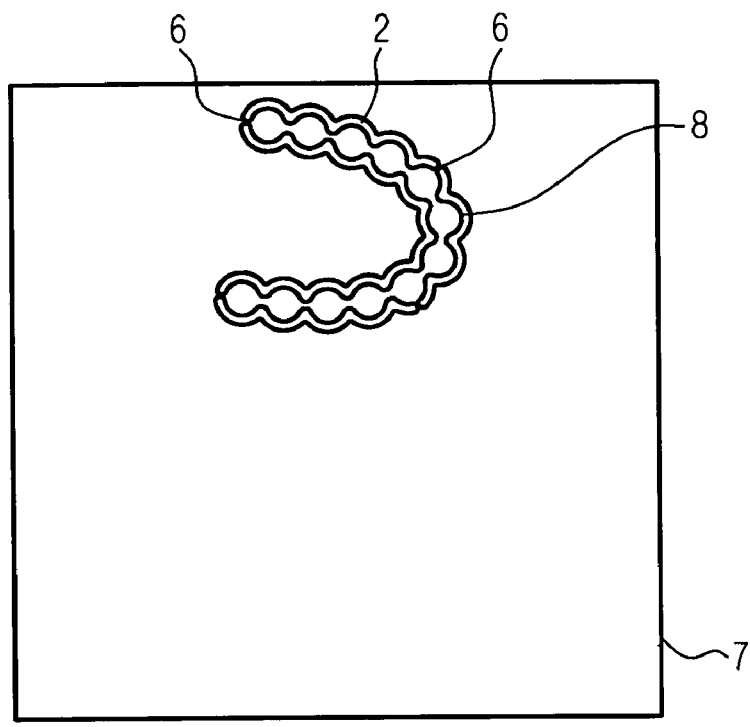
FIG. 2 shows a milling position of a dental prosthesis on a blank.

In FIG. 2, one example of an arrangement of a milling shape on a blank 7 is shown. Here, the blank is of square shape, however, other shapes can also be provided, such as round, rectangular and otherwise shaped blanks.

A dental prosthesis 2, which is designed by way of example as twelve-membered dental prosthesis 2 in FIG. 2, is surrounded by a marginal milling area 8. Furthermore, webs 6 are drawn which serve for connecting the dental prosthesis 2 with the blank 7 during and after the milling procedure. Here, the blank 7 is clearly larger than the milling shape. Therefore, the milling shape can be arranged on the blank 7 in various orientations. In the process, the arrangement represented in FIG. 2 can be changed by shifting the milling shape upwards, downwards, to the right or to the left, or by rotating it, simultaneously with or independent of such a shifting, to the right or to the left. A tilt about an axis, for example situated in the blank plane, is also possible. In the method, the milling position is determined on the basis of predetermined criteria to obtain an optimised method.

The blank 7 can be designed such that it is altogether accessible to the milling machine with its surface. However, blank shapes where only one portion of the blank at a time is accessible to the milling machine can also be taken into consideration. The other portions of the blank can be made accessible by pushing the blank into the area of the milling machine. Here, the blanks advantageously have the shape of long rods.

Figure 3:
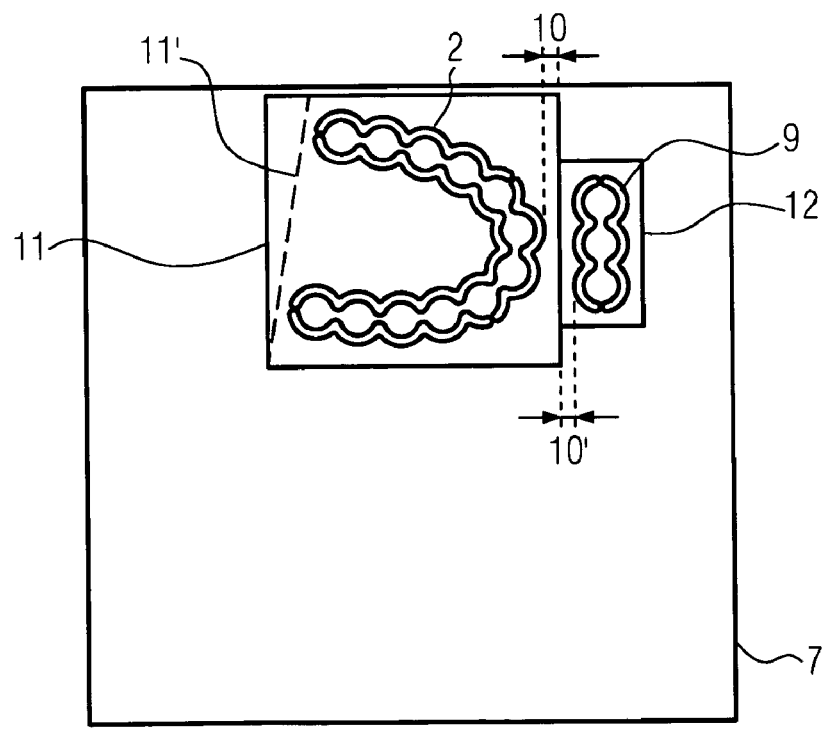
FIG. 3 shows the milling positions of two dental prostheses on a blank.
Figure 4:
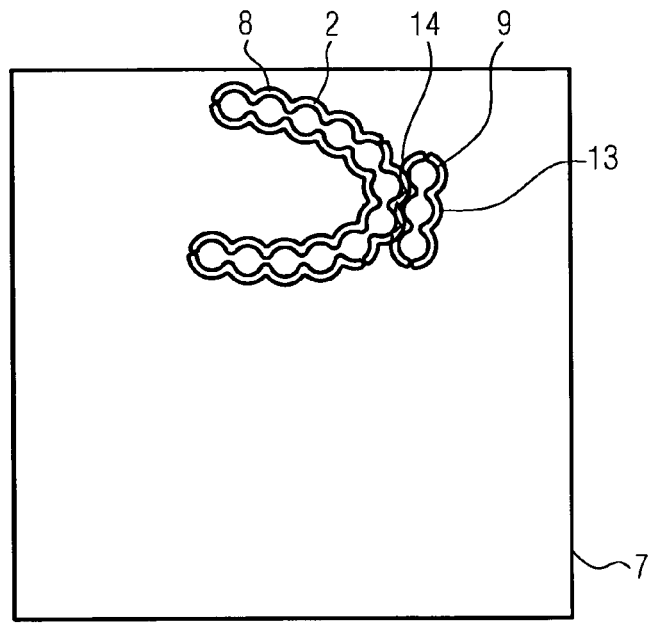
FIG. 4 shows the milling positions of two dental prostheses with another arrangement on a blank.

In FIGS. 3 and 4, a case is depicted where two milling shapes of two dental prostheses 2, 9 are to be accommodated on one blank.

In FIG. 3, a case is depicted where a bounding box 11 is arranged around the milling area of the dental prosthesis 2. The bounding box 11 here has a distance 10 to the respective extreme ends of the boundary of the marginal milling area 8. Here, the bounding box 11 is right-angled, however, it can also be arranged with an oblique angle, as shown by line 11'. Instead of four-cornered, one can also use three-, five-, six-, seven-, or eight-cornered, or round, elliptic or otherwise shaped bounding boxes. The bounding box 11 here only serves for determining the position of the dental prosthesis 9.

The dental prosthesis 9 is also surrounded by a bounding box 12 which was also constructed such that a minimum distance 10' between the outer boundary of the milling shape and the line of the bounding box 12 is observed.

The distance 10 and 10' can also be zero. However, a value other than zero ensures that between the dental prosthesis 2 and the dental prosthesis 9, blank material of at least the width corresponding to the values 10 and 10' remains. This ensures a certain desired stability of the blank 7 after the milling out of the dental prostheses 2 and 9.

The two bounding boxes 11 and 12 are arranged relative to one another such that they are coincident at one boundary line.

However, it is also possible to keep a minimum distance between the bounding boxes of two dental prostheses. This can also ensure a minimum distance between two dental prostheses which can be relevant for the stability of the blank 7 after the milling out.

In the method of determining the milling position, first the data of the dental prostheses 2, 9 are evaluated for determining respective bounding boxes 11, 12. Subsequently, the bounding boxes 11, 12 are arranged on the blank 7 relative to one another according to predetermined criteria. These criteria can be, for example, to fill the whole surface of the blank 7 with bounding boxes, if possible, which is best performed by having the bounding boxes overlap at their boundary lines.

Another method of determining the milling position is shown in FIG. 4. Here, no bounding boxes are determined; instead the milling positions are arranged directly on the blank 7 without the intermediate step via the bounding boxes.

The milling positions of the dental prostheses 2, 9 can here be arranged relative to one another such that the outer boundaries of the marginal milling areas 8, 13 slightly contact each other. However, as in the marginal milling areas 8, 13 there is no material apart from the webs 6, the marginal milling areas 8 and 13 can even overlap (see area 14). By passing the milling tool through the respective marginal milling area 8, 13, neither the dental prosthesis 2 nor the dental prosthesis 9 is damaged. The respective marginal milling areas 8, 13, however, must not overlap the area of the dental prosthesis 2, 9 or the respective webs. Instead of an overlap or a contact of the marginal milling areas 8, 13, a minimum distance from the marginal milling areas 8, 13, can be predetermined.

As can be seen when comparing FIGS. 3 and 4, the different arrangement of the milling areas of the dental prostheses 2 and 9 result in different shapes and/or remaining sizes of the milled surface of the blank 7. From the blank 7 in FIG. 4, more dental prostheses can be milled out than from the blank 7 in FIG. 3, as here the distance between the milling areas is larger. On the other hand, the blank in FIG. 3 has a higher stability compared to the blank of FIG. 4 where no web-like connection remains between the dental prostheses 2 and 9.

When determining the milling positions of the dental prostheses 2 and 9, a sufficient distance to the margin of the blank 7 is also considered.

Figure 5:
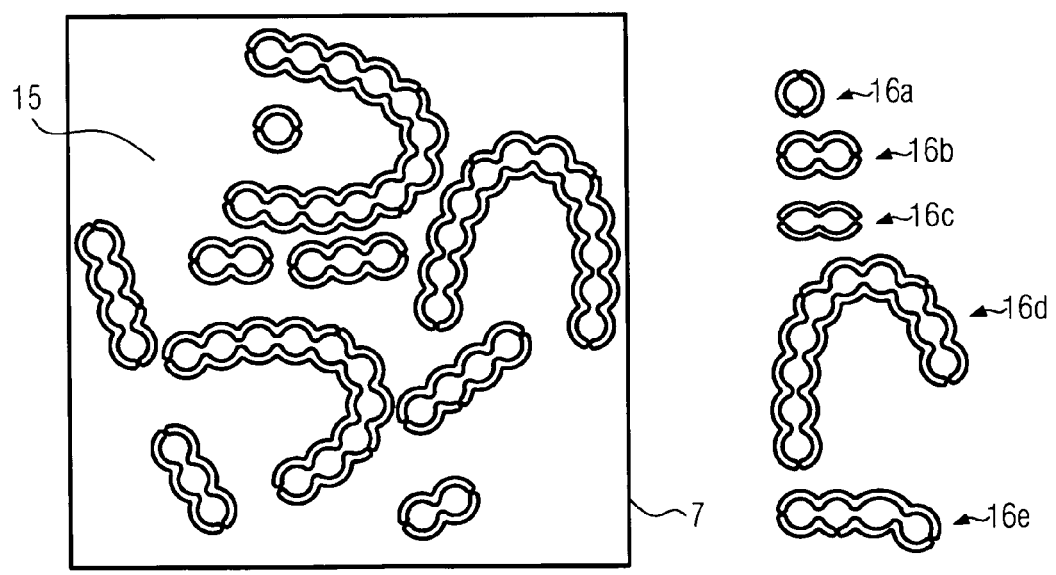
FIG. 5 shows the arrangement of several dental prostheses on a blank as well as several milling shapes.

In FIG. 5, a blank 7 is shown. The milling shapes drawn on the blank 7 can either be planned milling positions or already milled out areas. In the area 15 of the blank 7, there is still some space for the milling position of another dental prosthesis. In FIG. 5, various milling shapes are shown on the right. The milling shapes shown on the right in FIG. 5 can be, for example, milling shapes of dental prostheses still to be produced. However, they can also be predetermined standard shapes which approximately correspond to consistently occurring milling shapes of dental prostheses. On the right in FIG. 5, some shapes are represented by way of example only. Essentially more or less shapes are also possible.

In the method, one tries to arrange each of the shapes 16a to 16e in the area 15 of the blank 7. While this is certainly possible with the milling shapes 16a to 16c, the milling shape 16d will cause difficulties.

With the method, one can determine, for example, whether the blank 7 is full or not yet full. If none of the predetermined milling shapes can be accommodated on the blank 7, the blank is rated to be full and can therefore be rejected.

If the predetermined milling shapes are the milling shapes of dental prostheses to be manufactured, a maximum number of predetermined milling shapes can be preset. Thus, it can be reasonable, for example, not to consider more than 10, 20, 30, 40, 50 or 100 milling shapes to be manufactured. The more milling shapes are considered, the more elaborate the method will be, the more probable it will be, however, that there is a milling shape which can be still arranged on a blank that is nearly full.

In order to judge how well a blank 7 is utilized, for example, in FIG. 5 the surface which is unworked can be related to the worked surface.

Moreover, the various dental prostheses can be weighted. An n-membered dental prosthesis, for example, can be weighted with a value n or $n^2$ or the like, and subsequently, the sum of the weighted values can be determined in order to judge how well the blank 7 is utilized. Multi-membered dental prostheses necessarily require more space, so that a higher weighting is reasonable. The higher the sum, the better the utilization is.

Figure 6:
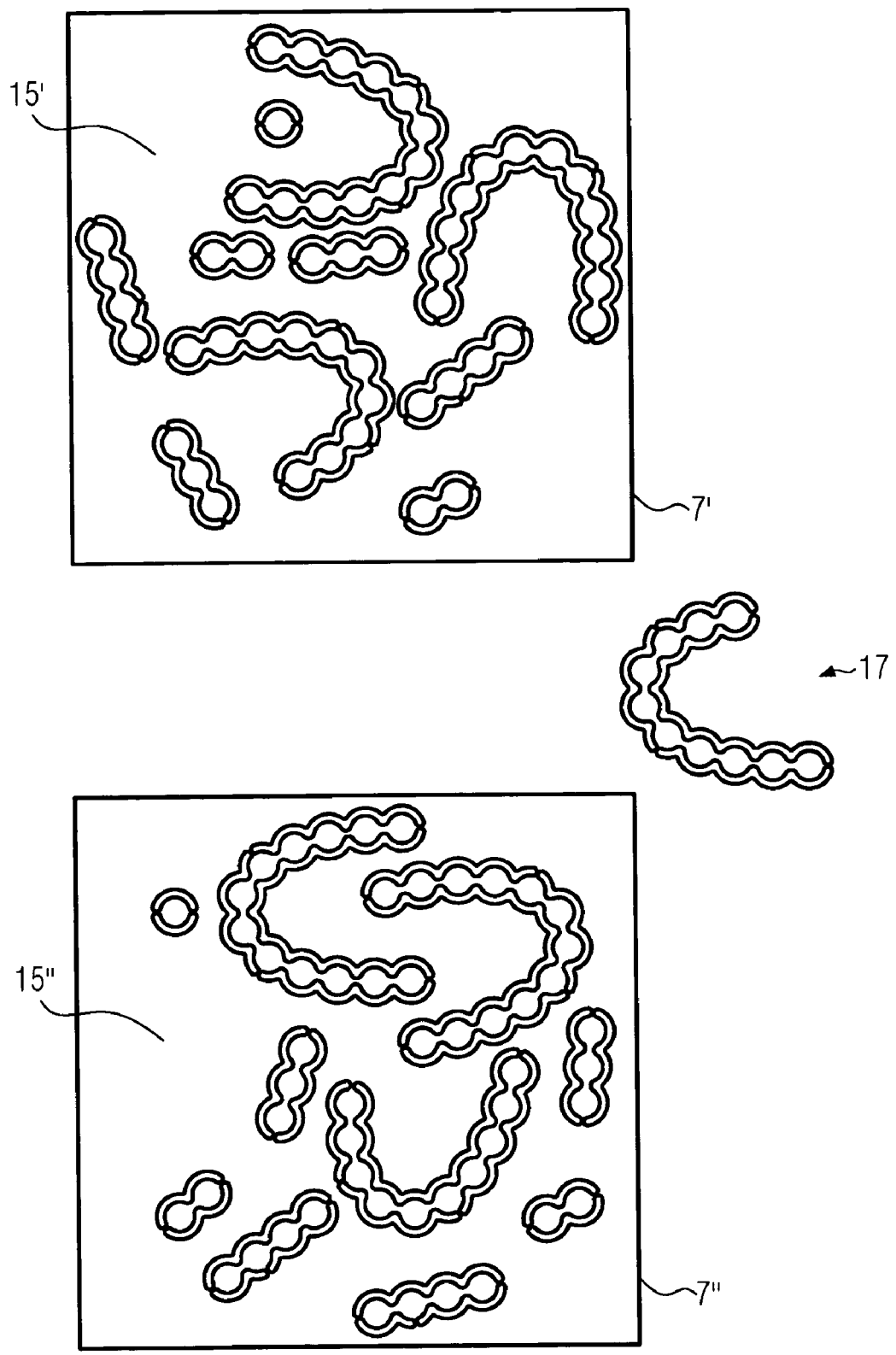
FIG. 6 shows several blanks and a milling shape.
Figure 7:
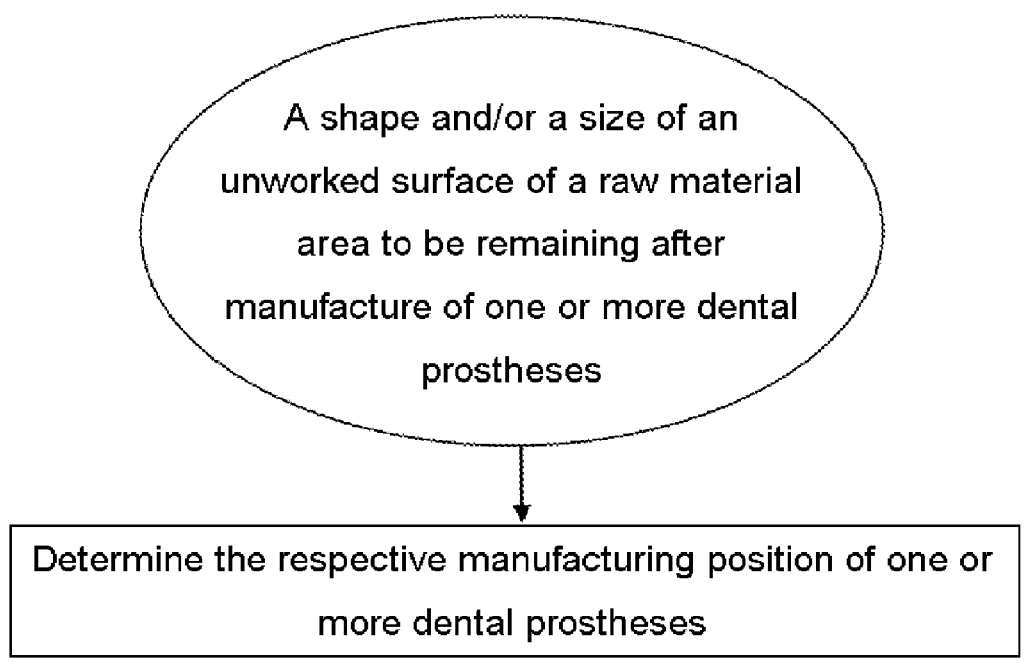
Figure 8:
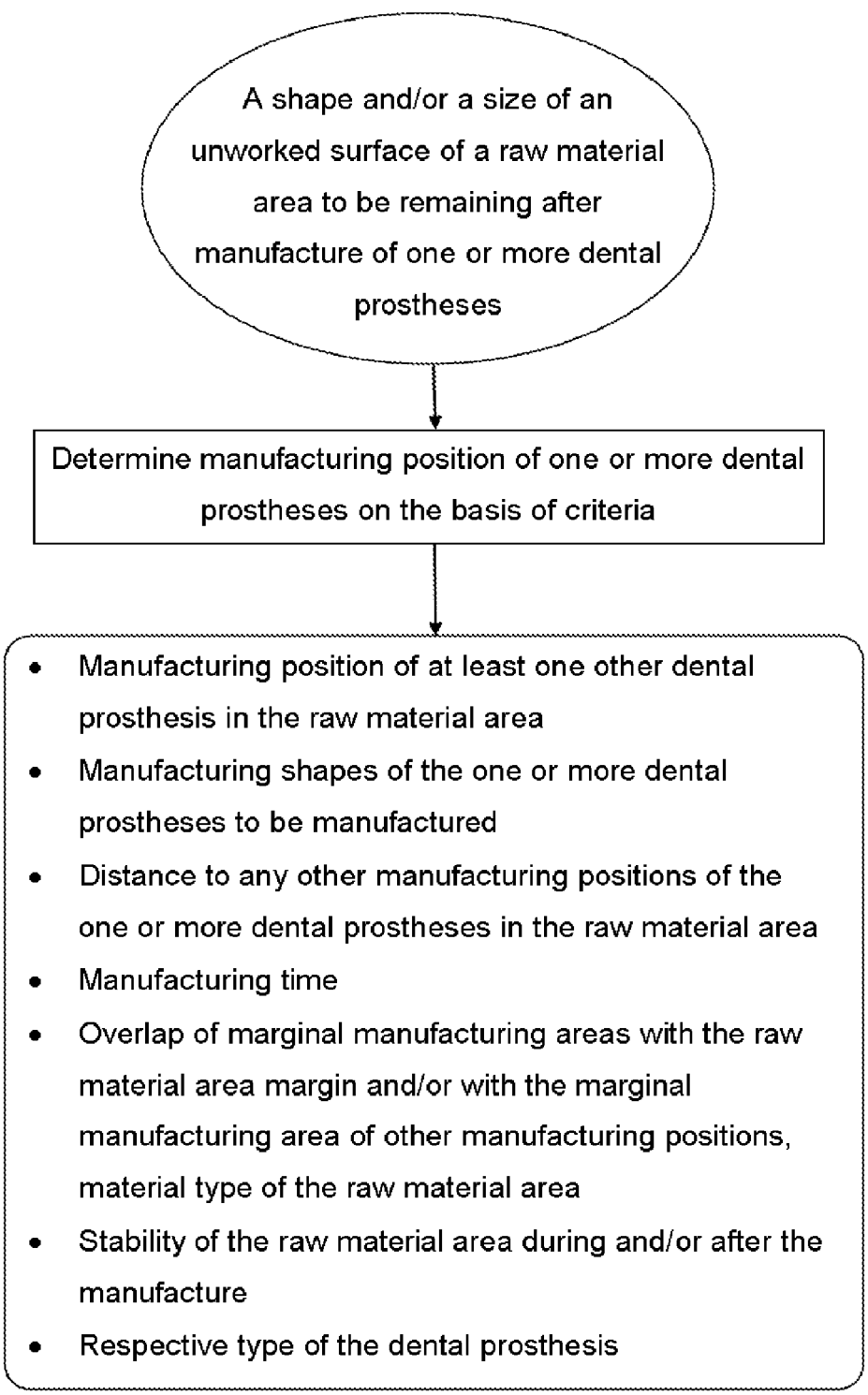
Figure 9:
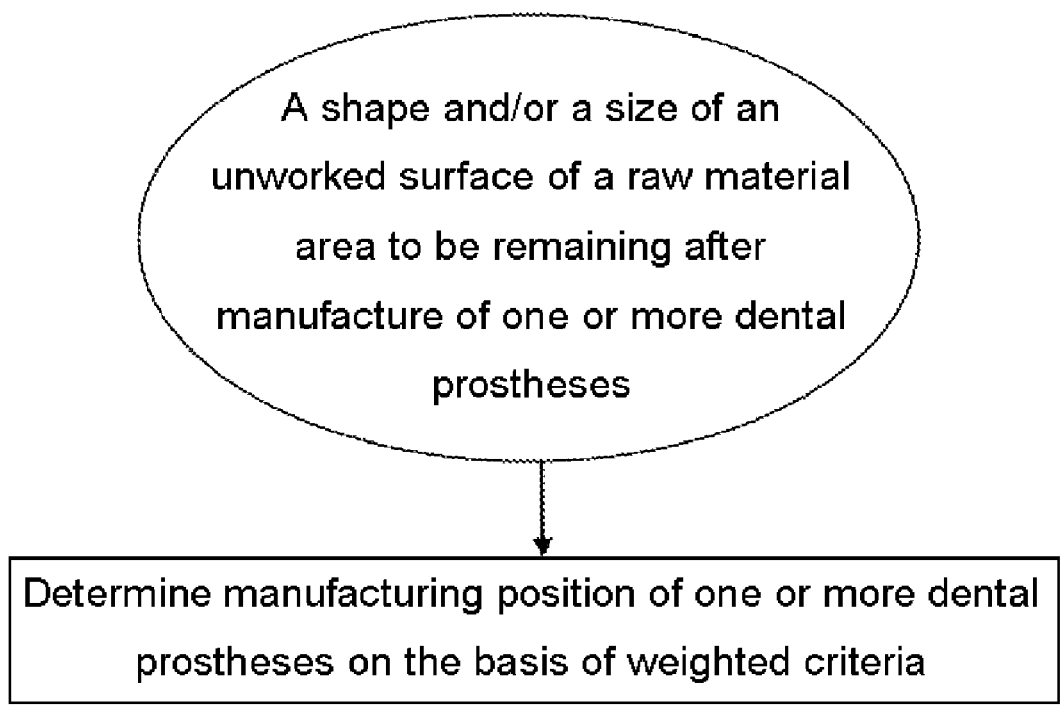
Figure 10:
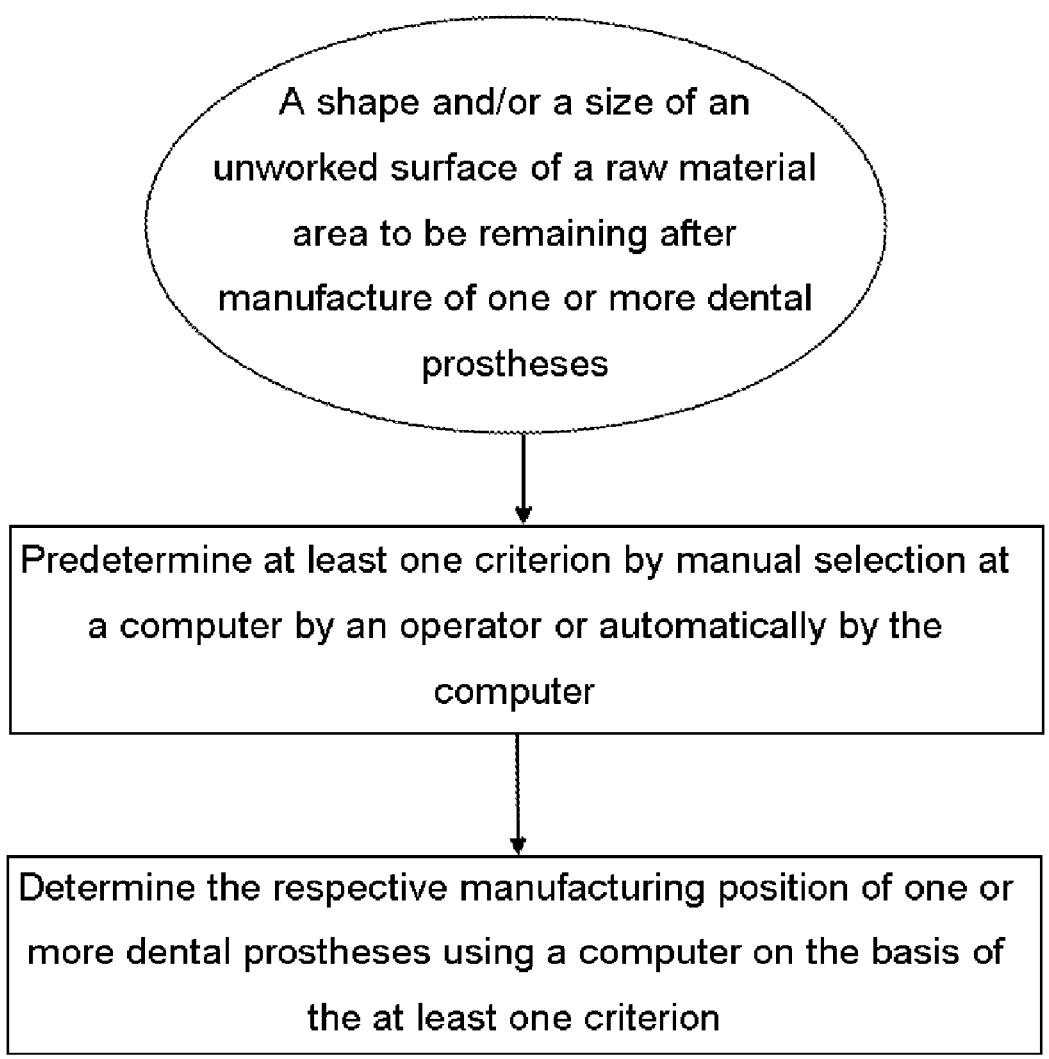
Figure 11:
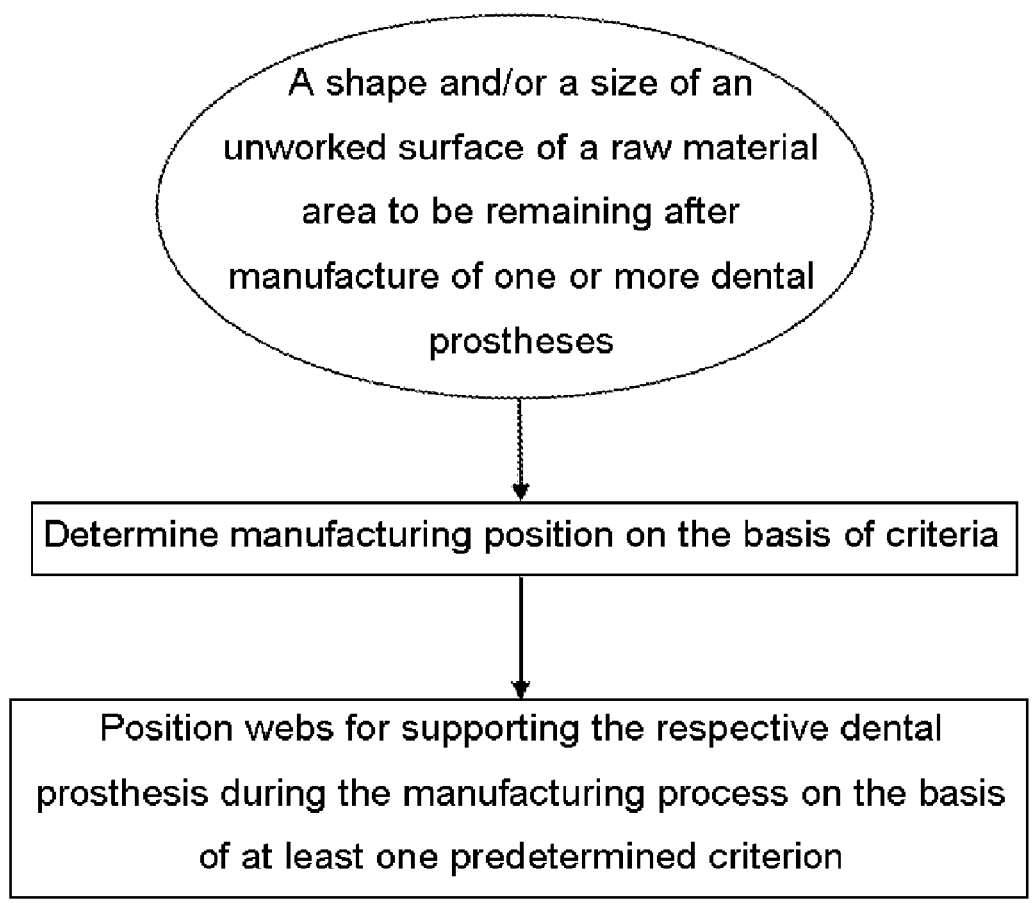
Figure 12:
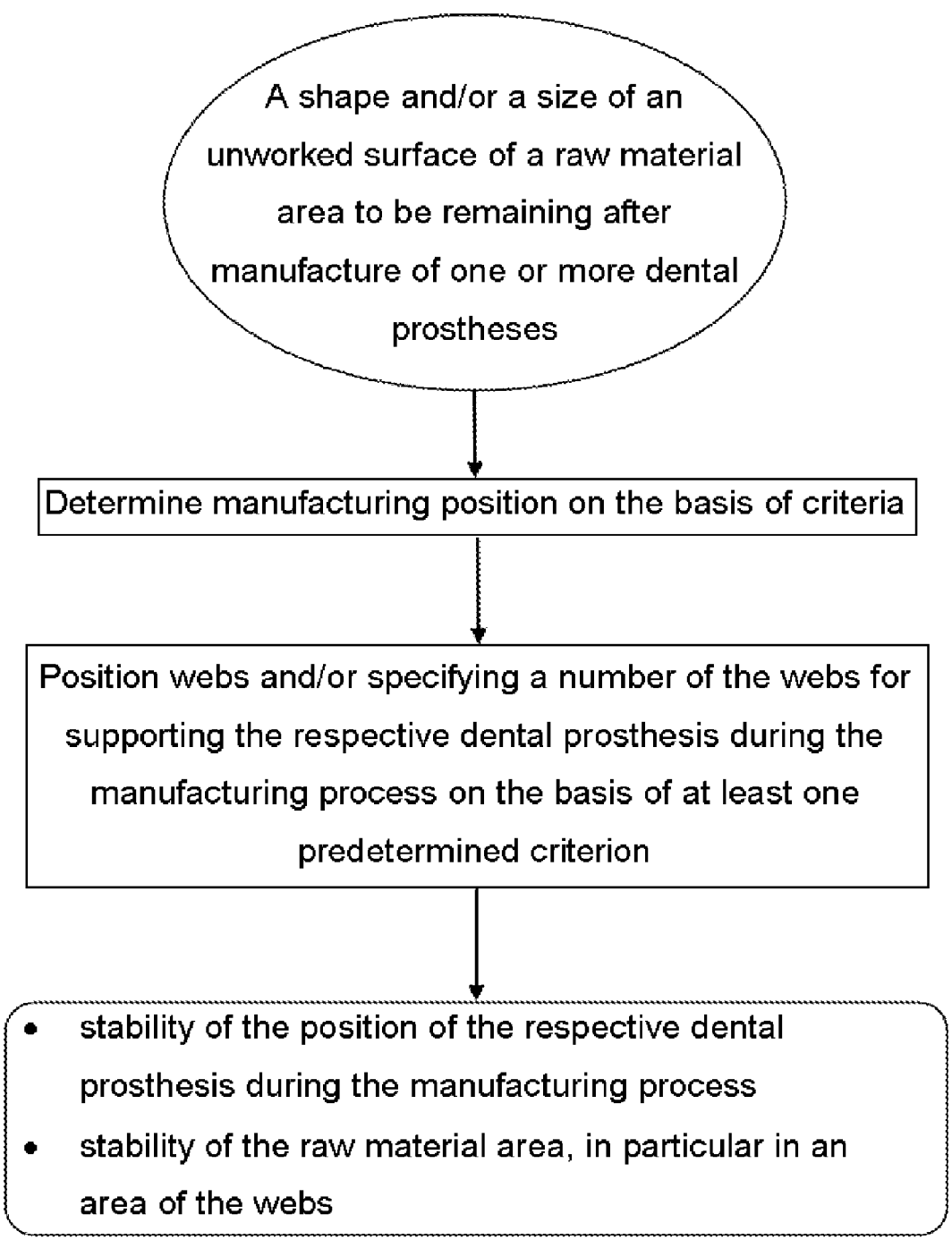
Figure 13:
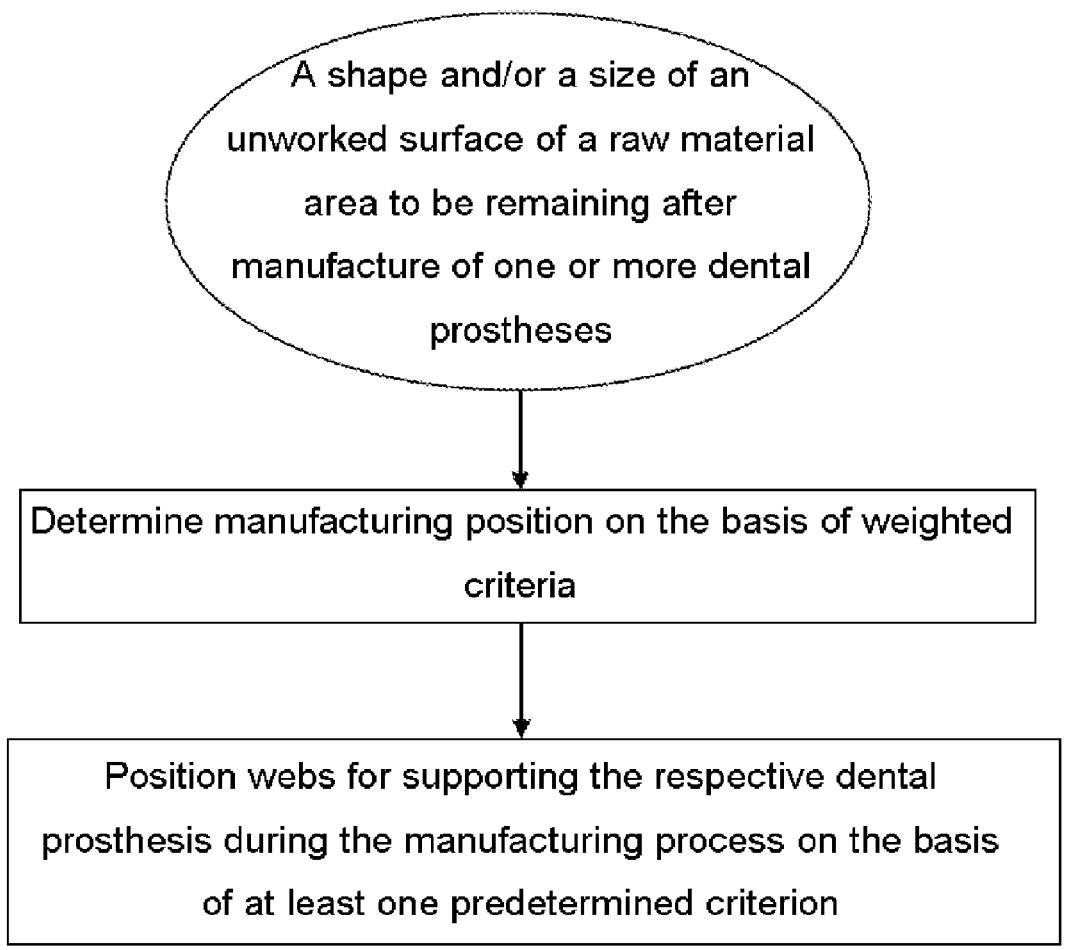
Figure 14:
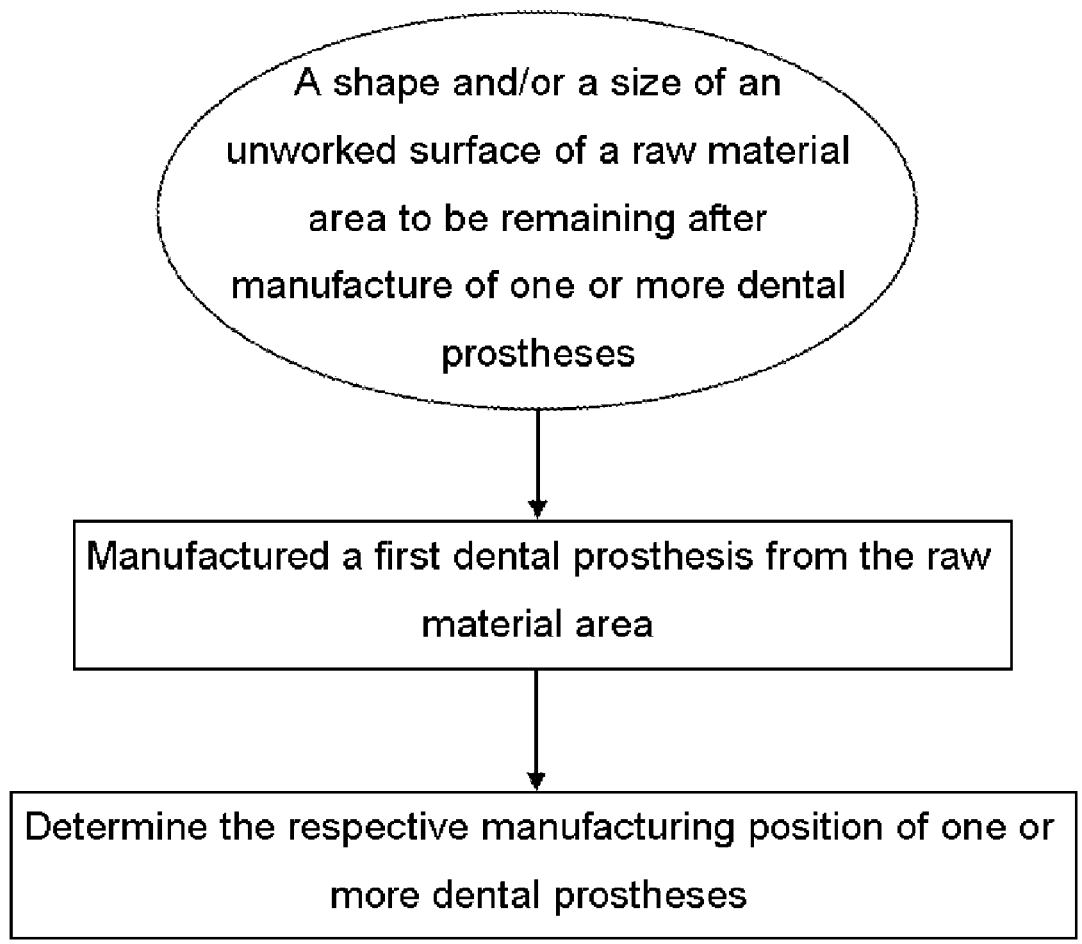
Figure 15:
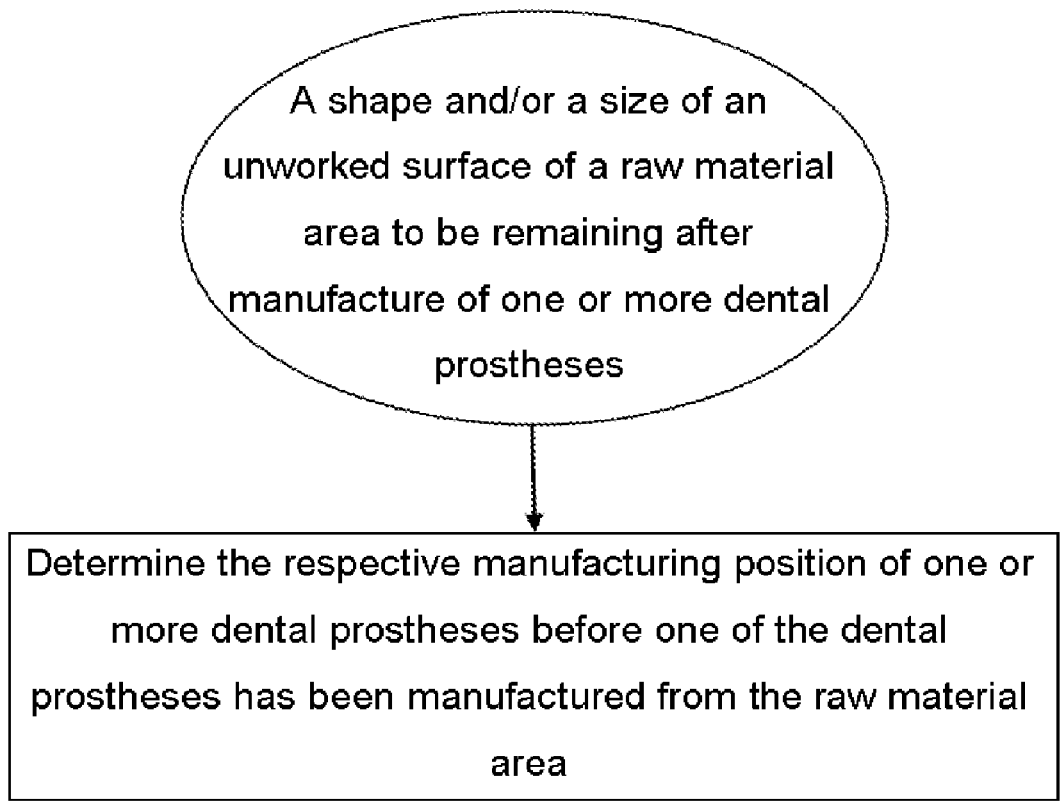
Figure 16:
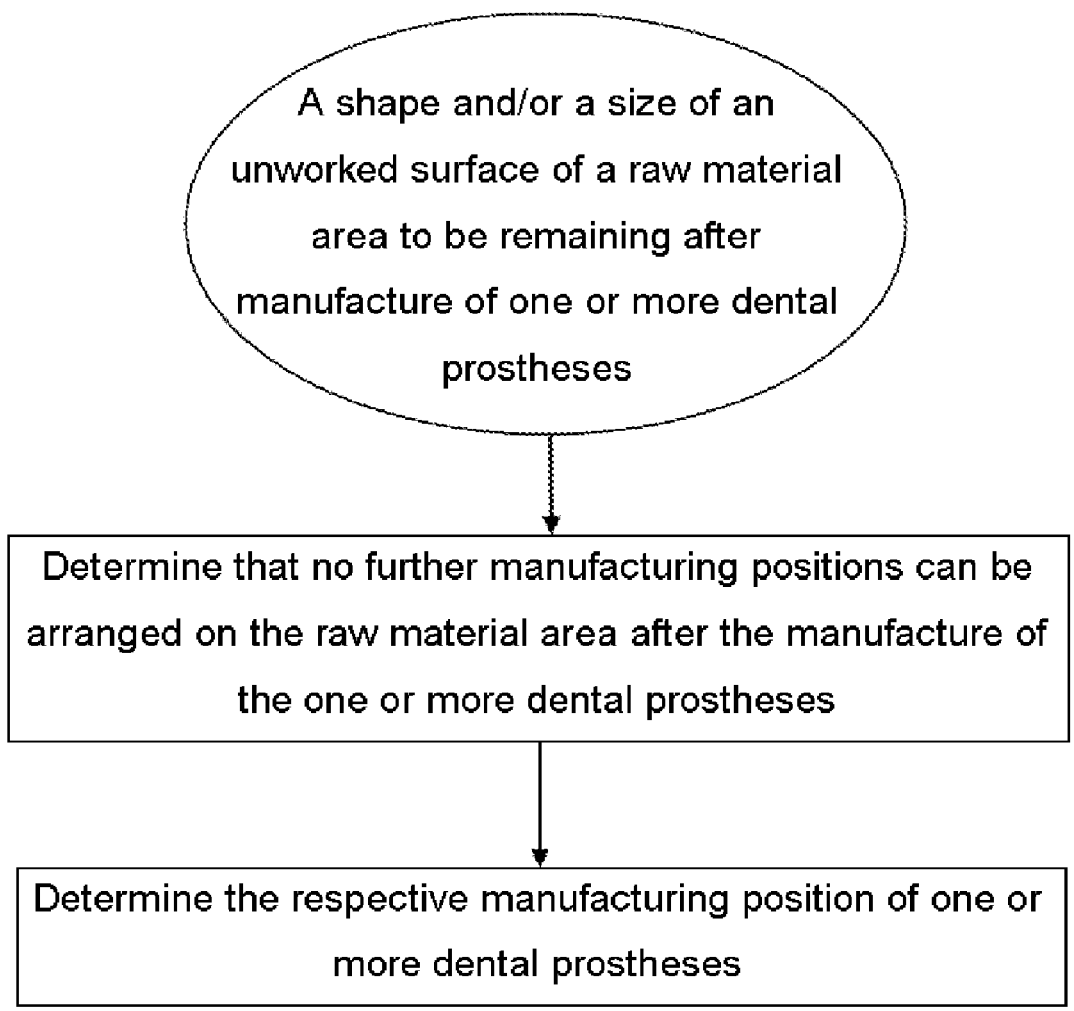
Figure 17:
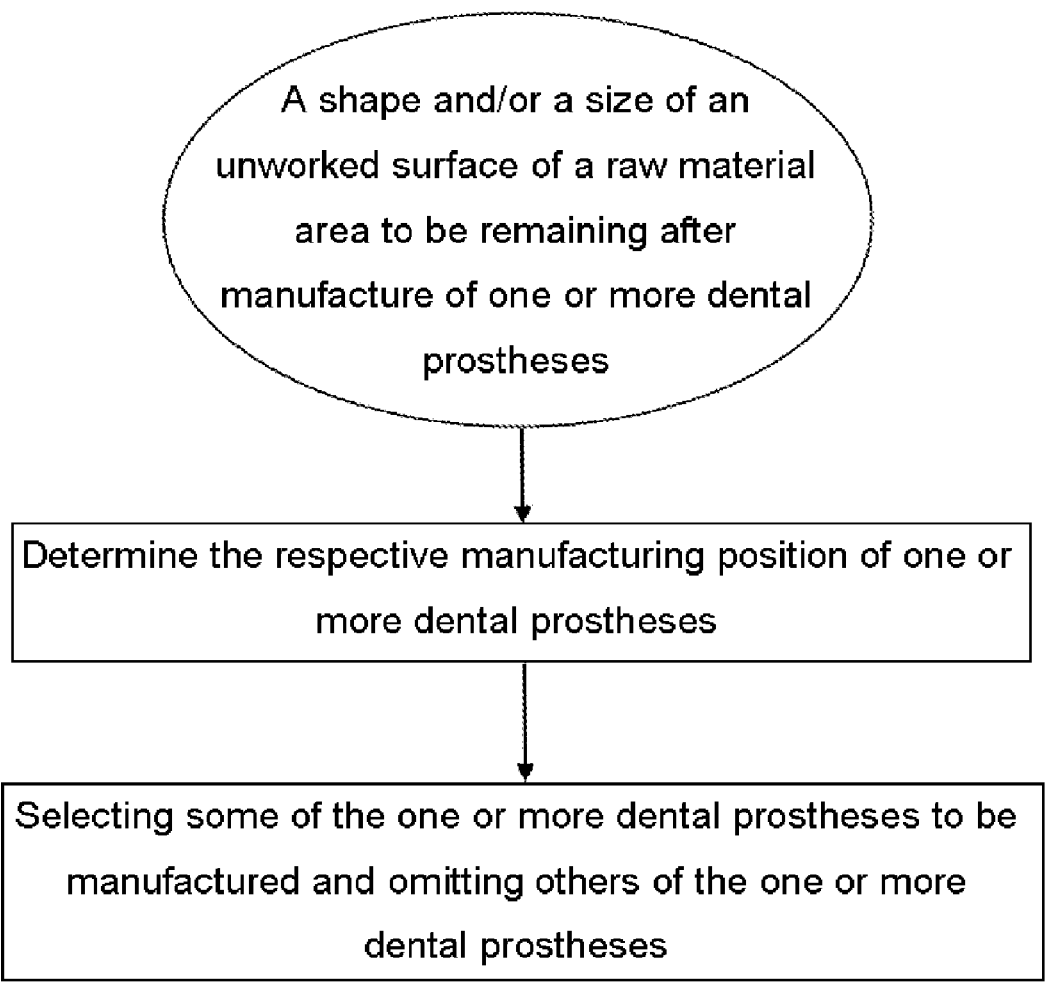
Figure 18:
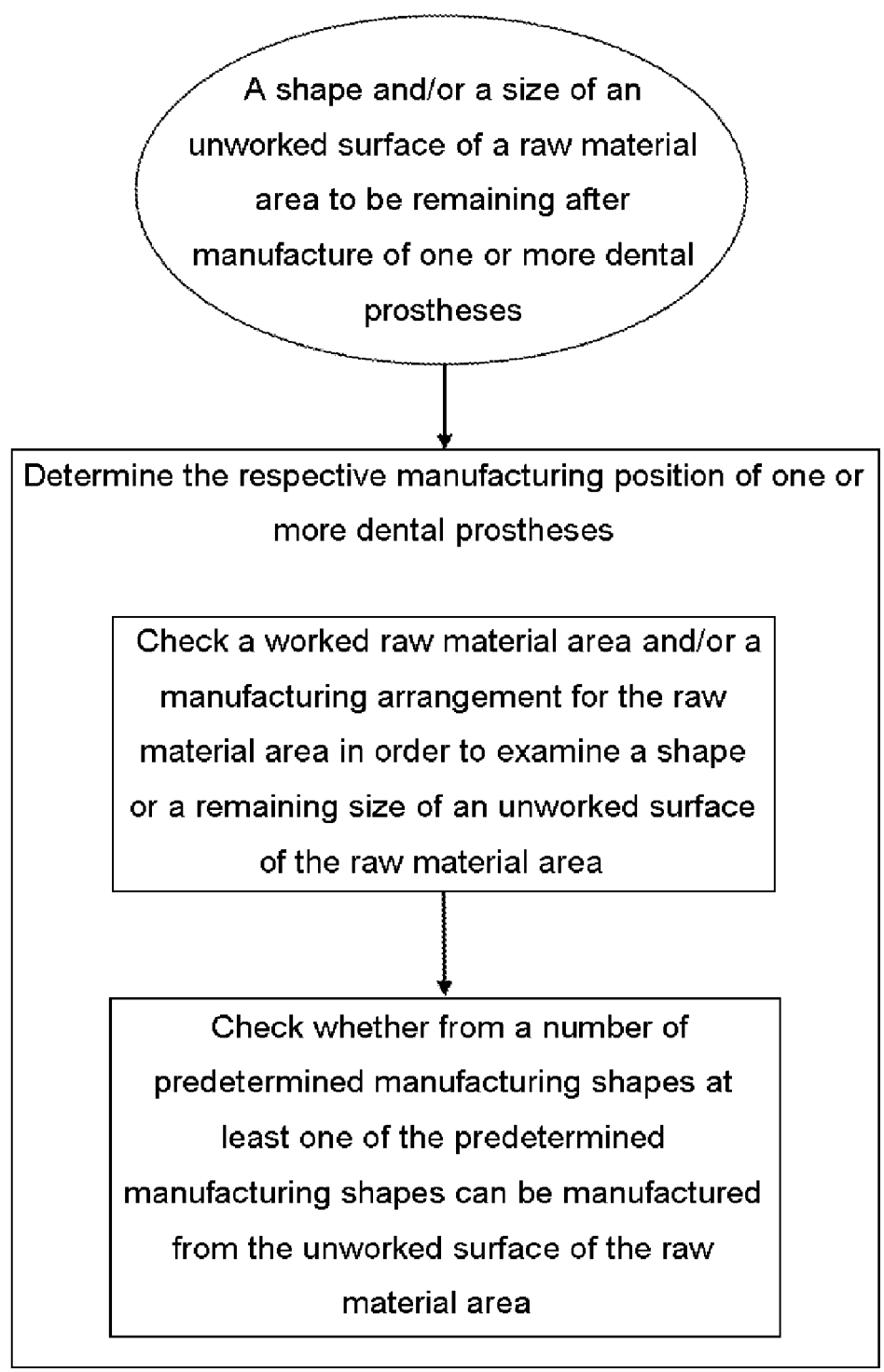
Figure 19:
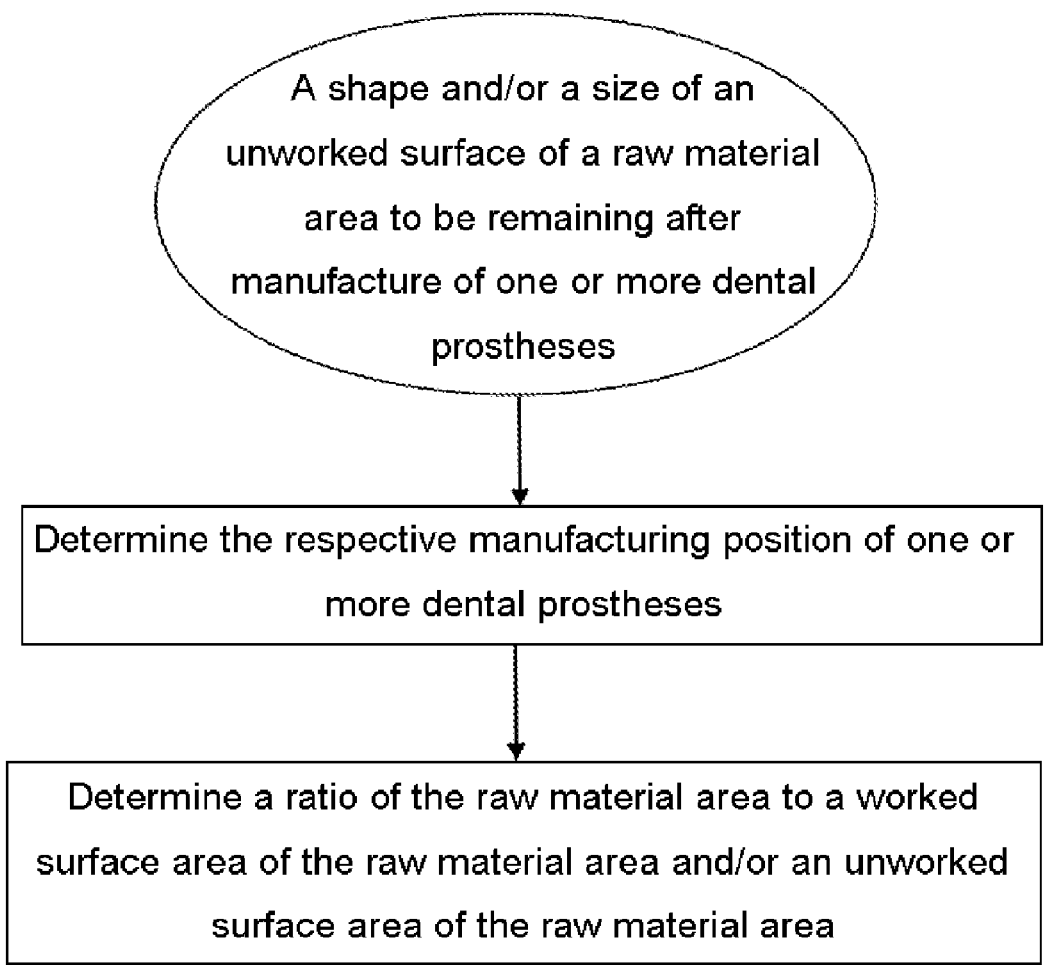
Figure 20:
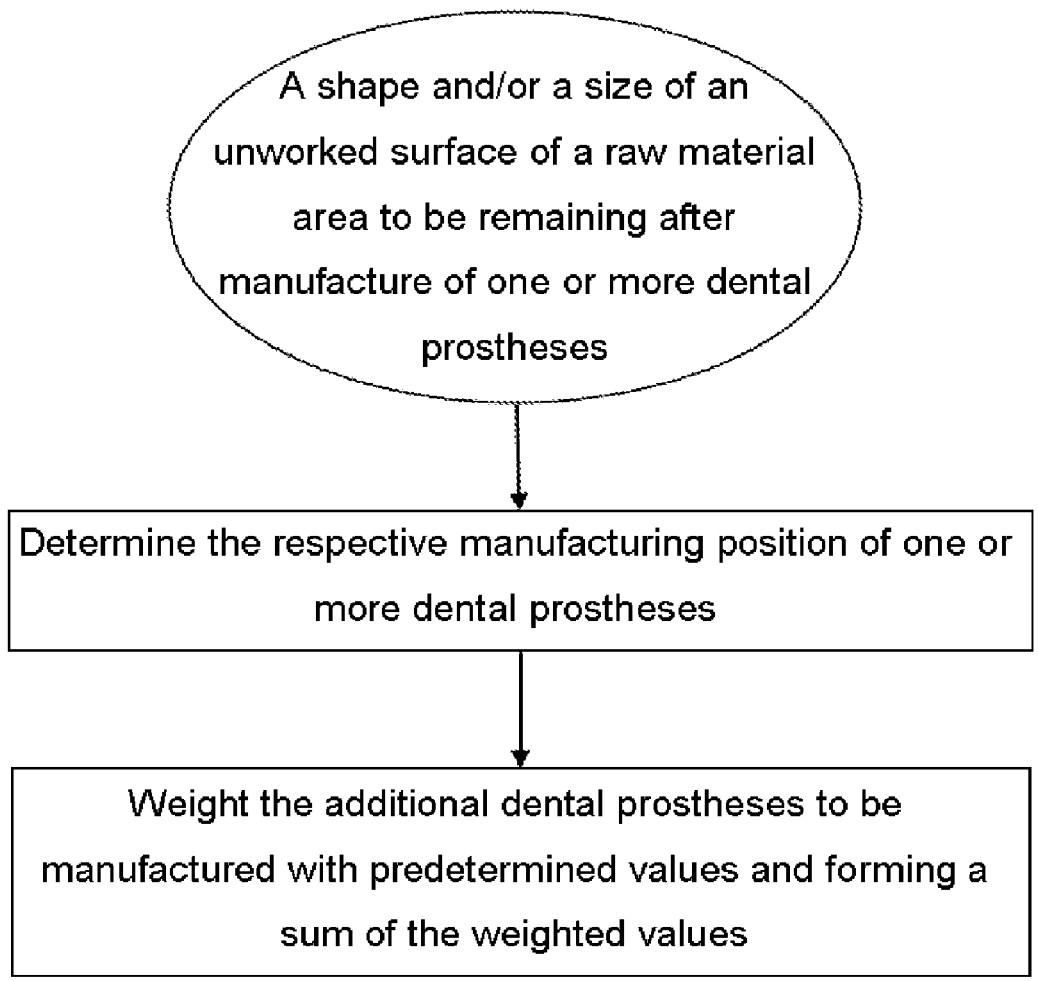
Figure 23:
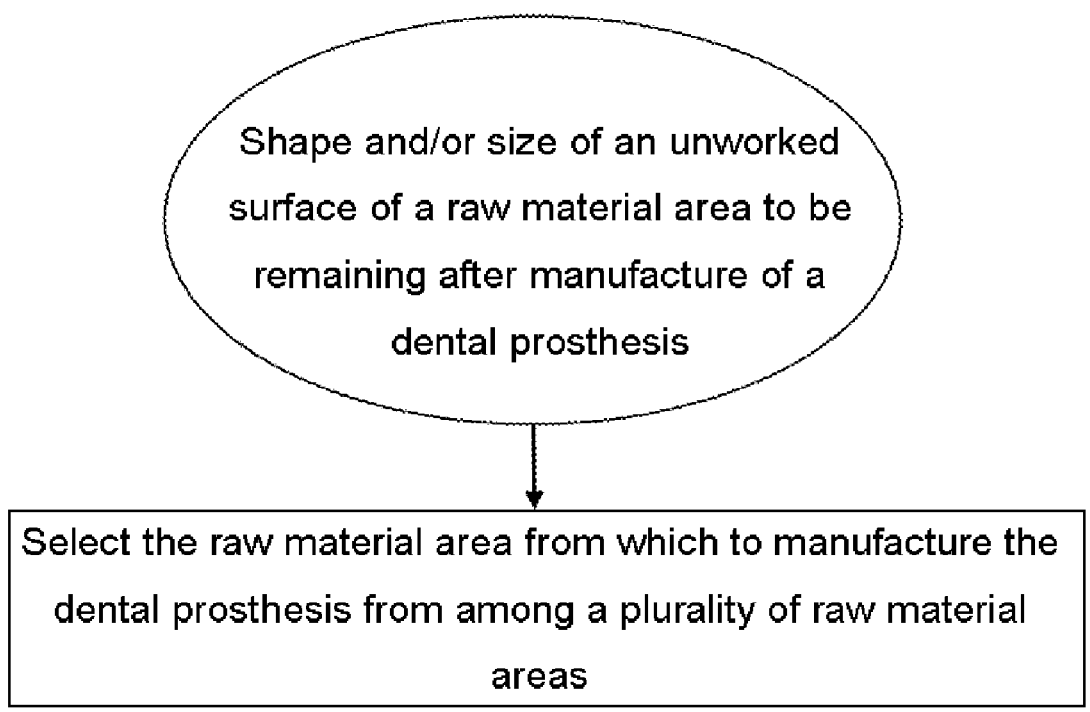
Figure 24:
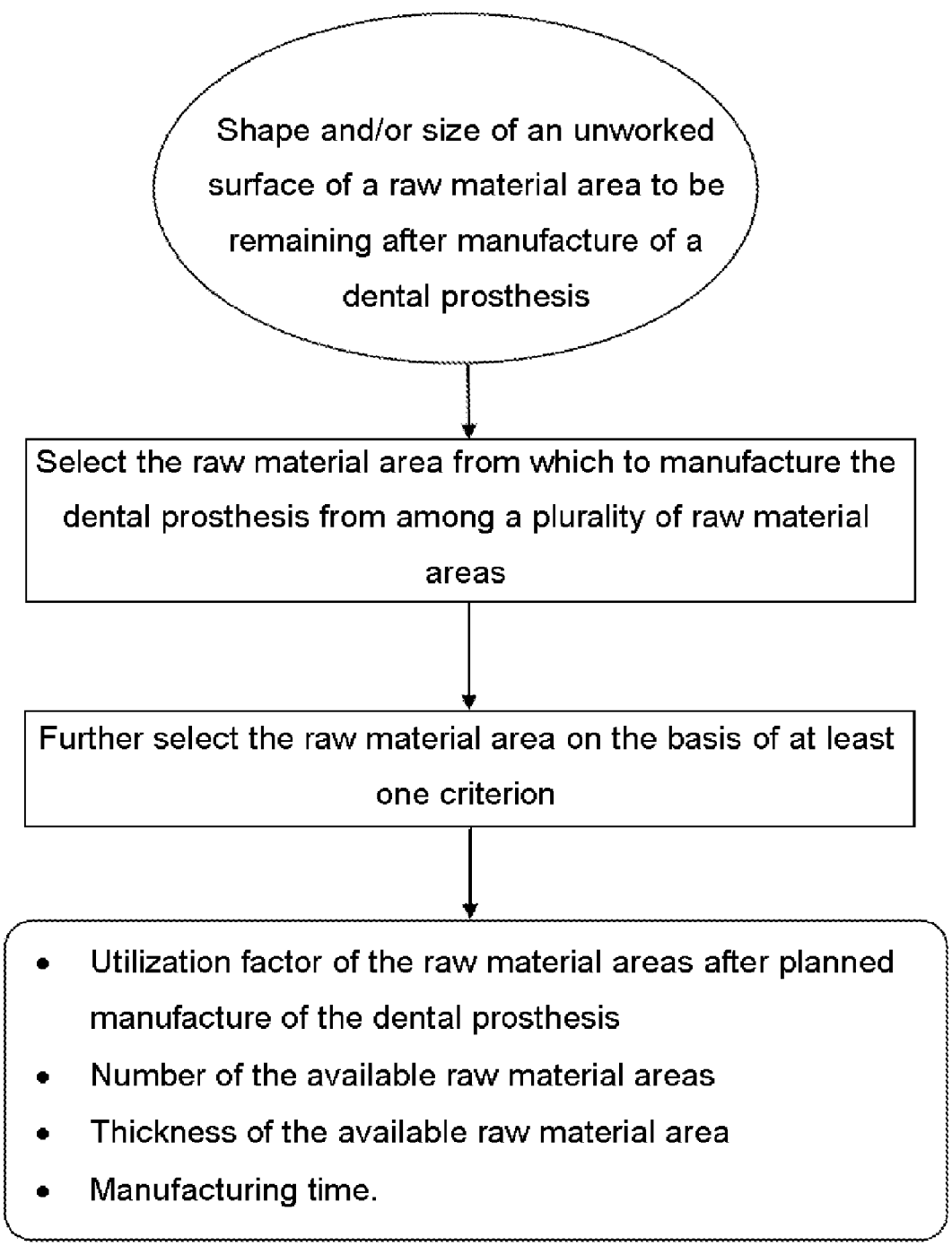
Figure 25:
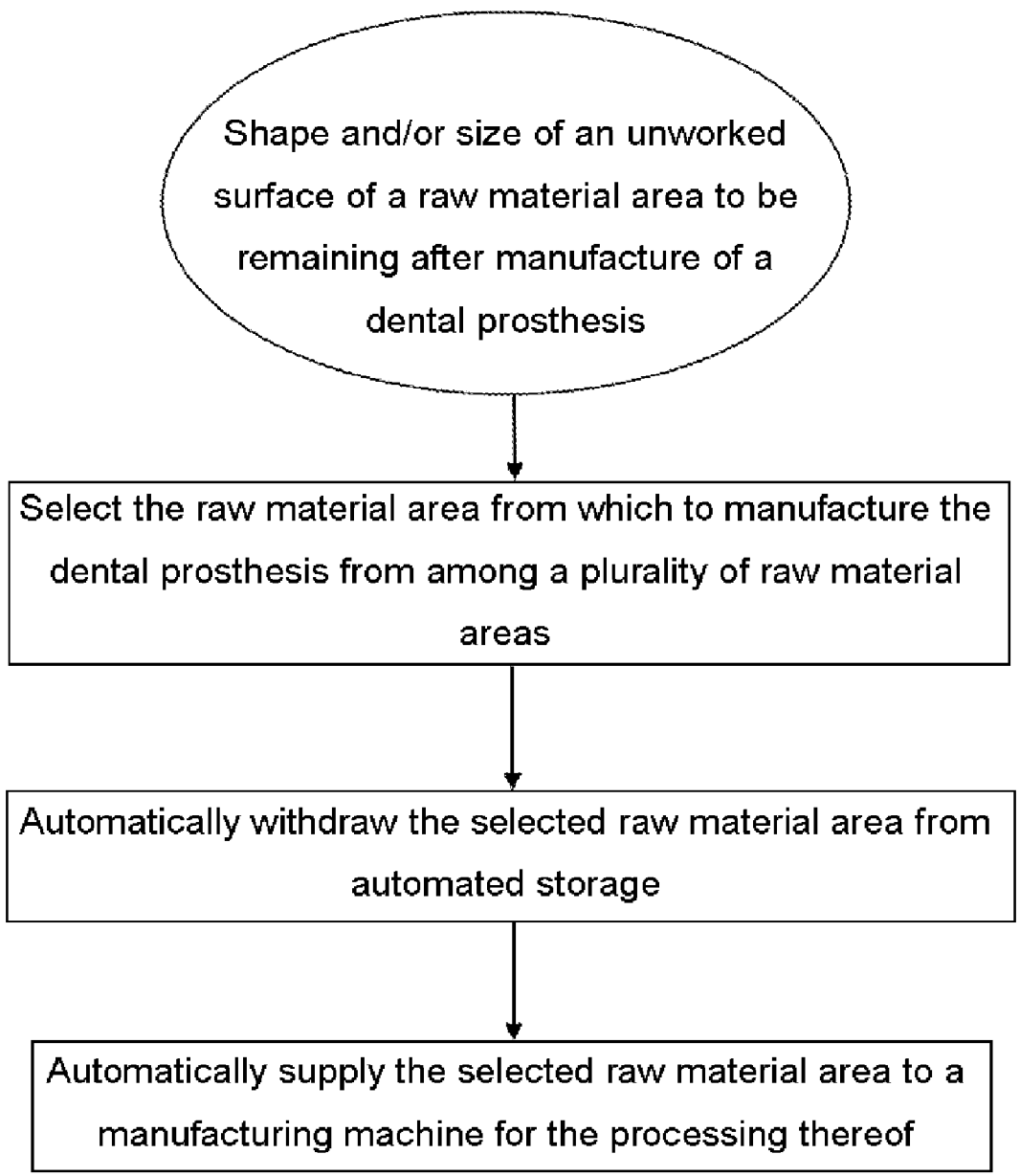
Figure 26:
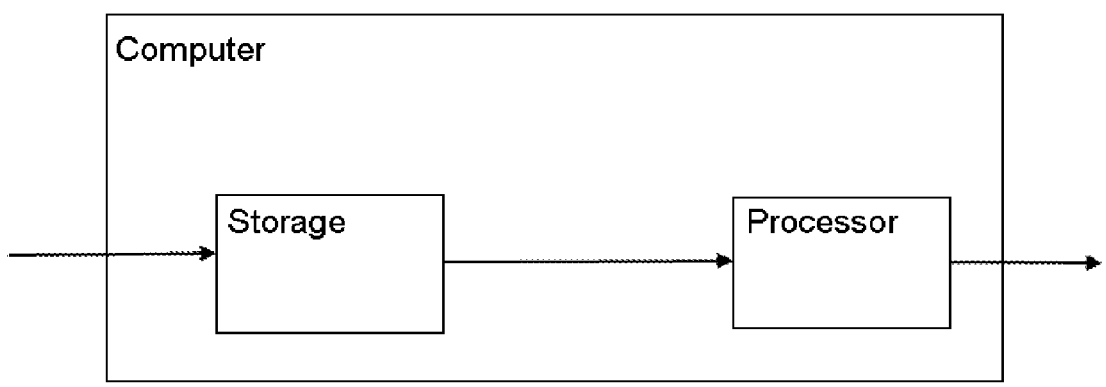
FIG. 26 is a block diagram of an exemplary computer system of the invention.

In FIG. 6, a case is depicted where two blanks 7' and 7" are available, which, however, both have an area 15' and 15" available from which dental prostheses can be milled out. The method will be illustrated with reference to the milling shape 17 by way of example. It is checked whether the milling shape 17 can be fitted into the area 15' of the blank 7' or in the area 15" of the blank 7". On the basis of these examinations, one of the two blanks 7', 7" is selected. Instead of two blanks, one can also consider at least or at most 10, 20, 30, 50 or 100 blanks. When selecting the blank, various criteria can be taken into consideration. For example, it can be optimal to select such a blank where a high utilization factor of the blank results with the arrangement of the milling shape 17. If a large number of blanks is available it can also be advantageous to utilize a blank that is subsequently rated as full in order to reject the blank and provide space for a new blank. The space is essentially predetermined by the storage capacities.

If the thickness of the available blanks varies, the thickness of the blanks can also be taken into consideration. Inherently, it is always reasonable to select the thinnest blank from which the dental prosthesis can be milled out, however, under certain circumstances it can also be advantageous to use a somewhat thicker blank if the same is then particularly well utilized, or it can then be e.g. disposed of.

The shape and/or remaining size of the blanks 7', 7" after the arrangement of the milling shape 17 can also be considered. The milling time can also be a criterion.

Instead of the selection of a blank on the basis of only one milling shape 17, one can also take into consideration two or more milling shapes.

The various blanks are best administrated in a blank data base. The latter stores, for example, a blank identification, the milled out areas or the not yet milled areas, as well as further data, such as age, storage time, etc. In the methods, software that executes the methods automatically accesses the blank data base in order to retrieve the information necessary for the various procedure steps.

The methods described herein can be easiest automatically executed by a computer. For doing so, a correspondingly equipped computer as well as a computer program or a machine-readable medium with instructions to be executed by the computer can be provided.

The invention claimed is:

1. Method for manufacturing dental prostheses from a raw material area at a manufacturing position, comprising:
    determining the respective manufacturing position of one or more dental prostheses on the basis of at least one of stability of the raw material area during the manufacture of the one or more dental prostheses and stability of the raw material area after the manufacture of the one or more dental prostheses.

2. Method according to claim 1, further comprising further determining the manufacturing position on the basis of at least one of the following criteria:
    manufacturing position of at least one other dental prosthesis in the raw material area,
    manufacturing shapes of the one or more dental prostheses to be manufactured,
    a shape of an unworked surface of the raw material area to be remaining after the manufacture of the one or more dental prostheses,
    a size of the unworked surface of the raw material area to be remaining after the manufacture of the one or more dental prostheses,
    distance to any other manufacturing positions of the one or more dental prostheses in the raw material area,
    manufacturing time,
    overlap of marginal manufacturing areas with the raw material area margin or overlap of marginal manufacturing areas with the marginal manufacturing area of other manufacturing positions, and
    material type of the raw material area, and
    respective type of the dental prosthesis.

3. Method according to claim 2, further comprising applying weighting factors to the criteria, and taking into consideration the weighting factors when a plurality of the criteria are used when determining the respective manufacturing position.

4. Method according to claim 2, wherein determining the manufacturing position includes using a computer, such that the at least one criterion is predetermined by manual selection at the computer by an operator or automatically by the computer.

5. Method according to claim 2, further comprising positioning of webs for supporting the respective dental prosthesis during the manufacturing process on the basis of at least one said criterion.

6. Method according to claim 5, further comprising at least one of positioning the webs and specifying a number of the webs on the basis of the at least one criterion, wherein the at least one criterion includes at least one of:
    stability of the position of the respective dental prosthesis during the manufacturing process, and
    stability of the raw material area, in particular in an area of the webs.

7. Method according to claim 6, further comprising applying weighting factors to all the criteria, and taking into consideration the weighting factors when a plurality of the criteria are used when determining the respective manufacturing position.

8. Method according to claim 1, further comprising determining the manufacturing position after a previous dental prosthesis has already been manufactured from the raw material area.

9. Method according to claim 1, further comprising determining the manufacturing positions of the one or more dental prostheses before one of the dental prostheses has been manufactured from the raw material area.

10. Method according to claim 1, further comprising selecting some of the one or more dental prostheses to be manufactured and omitting others of the one or more dental prostheses, to achieve a higher utilization of the raw material area than if one or more of said omitted dental prostheses would have been selected instead of one or more of said selected dental prostheses.

11. Method according to claim 1, wherein determining the respective manufacturing position includes
    checking a worked raw material area or a manufacturing arrangement for the raw material area in order to examine a shape or a remaining size of an unworked surface of the raw material area, and
    checking whether from a number of predetermined manufacturing shapes at least one of the predetermined manufacturing shapes can be manufactured from the unworked surface of the raw material area.

12. Method according to claim 1, further comprising determining at least one of a ratio of the raw material area to a worked surface area of the raw material area and a ratio of the raw material area to an unworked surface area of the raw material area.

13. Method according to claim 1, further comprising weighting additional dental prostheses to be manufactured with predetermined values and forming a sum of the weighted values.

14. Method for manufacturing a dental prosthesis from a raw material area, comprising:
    selecting the raw material area from which to manufacture the dental prosthesis from among a plurality of raw material areas, wherein the selection is made on the basis of a number of the plurality of raw material areas.

15. Method according to claim 14, further comprising further selecting the raw material area on the basis of at least one of the following criteria:
    utilization factor of the raw material areas after planned manufacture of the dental prosthesis,
    thickness of the available raw material area,
    shape of an unworked surface of the raw material area to be remaining after the manufacture of the dental prosthesis,
    size of an unworked surface of the raw material area to be remaining after the manufacture of the dental prosthesis, and
    manufacturing time.

16. Method according to claim 14, further comprising automatically withdrawing the selected raw material area from an automated storage and automatically supplying the selected raw material area to a manufacturing machine for the processing thereof.

17. Computer having
    a device for storing data of at least one dental prosthesis, and
    means for determining a respective manufacturing position of the at least one dental prosthesis with respect to a raw material area on the basis of at least one of stability of the raw material area during manufacture of the at least one dental prosthesis and stability of the raw material area after manufacture of the at least one dental prosthesis.

18. Computer having
    a device for storing data of a dental prosthesis to be manufactured from a raw material area, and
    means for selecting a raw material area for manufacture of the dental prosthesis from a plurality of raw material areas on the basis of a number of the plurality of raw material areas.

19. Computer program including instructions for performing the method of claim 1 when the program is executed by a computer.

20. Machine-readable medium storing instructions to be executed by a computer for performing a method according to claim 1 when the instructions are executed by a computer.

21. Method according to claim 1, wherein the raw material area comprises an area of a blank.

22. Method according to claim 1, wherein manufacturing is performed by milling out.

23. Method according to claim 16, wherein the automatic withdrawing is performed using a robot arm or automated raw material area transport and storage devices.

24. Method according to claim 16, wherein the manufacturing machine is a milling machine.

* * * * *